United States Patent [19]

Albrecht et al.

[11] Patent Number: 5,015,263

[45] Date of Patent: May 14, 1991

[54] COMPOSITION FOR COLORING SKIN AND METHOD

[75] Inventors: Linda Albrecht, West Redding; Leszek J. Wolfram, Stamford, both of Conn.

[73] Assignee: Clairol Incorporated, New York, N.Y.

[21] Appl. No.: 231,732

[22] Filed: Aug. 12, 1988

Related U.S. Application Data

[63] Continuation of Ser. No. 737,749, May 28, 1985, abandoned.

[51] Int. Cl.$^5$ ............................................. C09B 00/00
[52] U.S. Cl. .......................................... 8/680; 8/406; 8/409; 424/63
[58] Field of Search ................ 8/467, 94.18, 680, 406, 8/409, 423; 428/913, 914, 146, 150, 149; 156/231, 234, 236, 240; 424/63

[56] References Cited

U.S. PATENT DOCUMENTS 2,120,552  6/1938  Ellis et al. ............................... 8/527
4,169,169  9/1978  Kitabatake .......................... 427/149

*Primary Examiner*—A. Lionel Clingman
*Assistant Examiner*—John F. McNally
*Attorney, Agent, or Firm*—Sandra M. Nolan

[57] ABSTRACT

A composition for coloring skin comprising a carrier containing an alcohol component consisting of an aromatic alcohol, an aliphatic alcohol or mixtures thereof and certain certified acid dyes, said composition having an acid pH equal to or less than 4.

4 Claims, No Drawings

COMPOSITION FOR COLORING SKIN AND METHOD

This is a continuing application of application Ser. No. 737,749 filed May 28, 1985, now abandoned.

BACKGROUND OF INVENTION

This invention relates to a compositions for coloring skin and to process that uses said compositions. More particularly, it relates to compositions and processes of the aforesaid type that employs certain certified dyes of the acid class which provide a skin coloring that results in high resistance to water and rub-off.

There is plethora of skin bronzing products available on the market. They vary from milky, colorless lotions to intensely tinted thick gels. The former are usually based on dihydroxy acetone which, on prolonged contact with the skin, develops a somewhat durable yellowish coloration, whereas the tinted versions contain mixtures of pigments and certified dyes to produce quite attractive tanning effects These however, suffer from high rub-off and offer no resistance to the action of water (rain, sea or sweat).

SUMMARY OF INVENTION

It has now been found that certain certified dyes of the acid class readily color skin when applied to the skin from a composition having a pH on the acid side containing a stain penetrating agent capable of altering the hydrophobic and/or hydrophilic character cf the skin. The color imparted to the skin is highly resistant to water and rub-off.

DETAILED DESCRIPTION OF INVENTION

One of the principle objects of the present invention is to provide compositions and processes for coloring and, particularly bronzing skin to give it an appearance of a sun tan. However, they have other useful applications. Thus, for example, they may be used to at least temporarily color unpigmented skin such as to camouflage vitiligo etc. The compositions and processes of this invention may be used to bring these unpigmented areas up to a level approximating the surrounding black skin. The compositions and processes of this invention may also be used when the chief object of their use is some degree of protection from UV radiation. In this case they will be functioning to provide some sun screening benefit.

As pointed out above a feature of this invention is the fact that the imparted skin color is highly resistant to being washed off by water or rubbed off. Yet, it can be controlled so that, for example, an artificial tan can be removed by a gentle soap scrub.

The artificial tanning or bronzing effect obtained herein is equivalent to that obtained from commercially available bronzers. However, in distinction to the latter the bronzing obtained with the present products and processes shows high resistance to water and rub-off. The bronzing intensity of this invention can be modified as desired. This can be done, for example, by repeated applications of the composition, by varying the time of application or the concentration of the dyes contained therein.

A number of certified acid dyes are known which are useful for the purposes of the present invention. These may be of the anthraquinone, triphenylmethane, monoazo or quinoline type. These may be employed alone or in combination depending upon the use to which the composition will be put. Usually, however, they will be used in combination to simulate naturally tanned or black skin as the case may be.

Table I below gives those dyes which have been found to be especially useful for the present purposes. For ease of expressions and claiming the D&C or FD&C nomenclature will be used to identify these dyes. This nomenclature is accepted in the CTFA Cosmetic Ingredient Dictionary, second edition, 1977, published by *The Cosmetic, Toiletry and Fragrance Association, Inc.*

TABLE 1
STRUCTURE OF CERTIFIED DYES

EXT. D & C VIOLET NO. 2
CAS Number: 4430-18-6
Empirical Formula:
$C_{21}H_{16}NO_2S.Na$
Definition: Ext. D & C Violet No. 2 is a color classed chemically as an anthraquinone color. It conforms to the formula:

FD & C BLUE NO. 1
CAS Number: 3844-45-9
Empirical Formula:
$C_{27}H_{36}N_2O_2S_3.2Na$
Definition: FD & C Blue No. 1 is a color classed chemically as a triphenylmethane color. It conforms to the formula:

D & C ORANGE NO. 4
CAS Number: 633-96-5
Empirical Formula:
$C_{16}H_{12}N_2O_4S.Na$
Definition: D & C Orange No. 4 is a color classed chemically as a monoazo color. It conforms to the formula:

FD & C YELLOW NO. 6
CAS Number: 2783-94-0
Empirical Formula:
$C_{16}H_{12}N_2O_7S_3.2Na$
Definition: FD & C Yellow No. 6 is a color classed chemically as a monoazo color. It conforms to the formula:

D & C YELLOW NO. 10
CAS Number: 8004-92-0
Definition: D & C Yellow No. 10 is a mixture of the disodium salt of the mono- and disulfonic acids of 2-(2-quinolyl)-1,3-indandione.

2-(2-Quinolyl)-1,3-indandione
CI 47005
Actual Structure Unknown

D & C GREEN NO. 5
CAS Number: 4403-90-1
Empirical Formula:
$C_{20}H_{22}N_2O_8S_2.2Na$
Definition: D & C Green No. 5 is a color classed chemically as an anthraquinone color. It conforms to the formula:

FD & C RED NO. 4
CAS Number: 4548-53-2

FD & C YELLOW NO. 5
CAS Number: 1934-21-0

TABLE 1-continued
STRUCTURE OF CERTIFIED DYES
Empirical Formula:
$C_{18}H_{18}N_3O_7S_2 \cdot 2Na$
Definition: FD & C Red No. 4 is a color classed chemically as a monoazo color. It conforms to the formula:
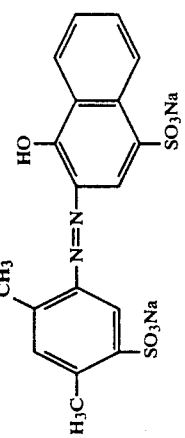
Empirical Formula:
$C_{16}H_{12}N_4O_8S_2 \cdot 3Na$
Definition: FD & C Yellow No. 5 is a color classed chemically as a pyrazole color. It conforms to the formula:
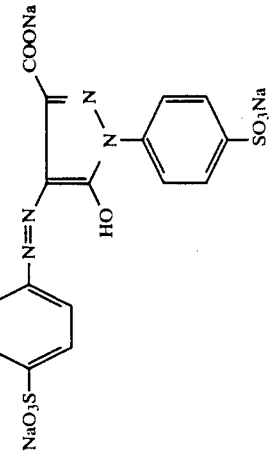

The quantity of certified acid dye which will be contained in the compositions of this invention will vary with a number of considerations such as the dye or dyes employed, the end use in mind etc. In general, however, the dye component (i.e. a single dye or combination of dyes) will constitute between about 0.01% and about 1% by weight based on the total weight of the composition with the preferred range being from about 0.05% to about 0.5% on the same weight basis.

As previously indicated in many, if not all, cases a combination of dyes will be utilized in practicing this invention. Exceptionally good results are obtained using a combination of Ext. D&C Violet No. 2, D&C Orange No.4 and FD&C Yellow No. 6 or the combination of Ext. D&C Violet No. 2, D&C Orange No. 4, FD&C Yellow No. 6 and FD&C Blue No. 1. Table II below gives the range of concentrations of the dyes which may be present in each type of composition. These are given as percent by weight based on the total weight of the composition.

TABLE II

|  | COMPOSITION A % by Weight | COMPOSITION B % by Weight |
|---|---|---|
| Ext. D & C Violet No. 2 | 0.035 | 0.05 |
| D & C Orange No. 4 | 0.30 | 0.16 |
| FD & C Yellow No. 6 | 0.025 | 0.025 |
| FD & C Blue No. 1 | 0.016 | 0.025 |

As indicated above it is a feature of this invention to incorporate in the compositions of this invention a skin penetrating agent which is capable of altering the hydrophobic, or hydrophilic characteristics of skin. These agents serve to increase the substantivity of the skin for the acid dyes utilized herein by changing the hydrophobic or hydrophilic character of the skin. Human skin is known to contain both hydrophobic and hydrophilic structural components. The skin penetrating agents of this invention change either or both of these structures so as to make the acid dyes of this invention more substantive to skin.

It has been found that a number of agents are capable of affecting the hydrophobic or hydrophilic character of skin. One such class of materials are the aromatic or aliphatic alcohols or combination of such alcohols. These will ordinarily be liquids and thus may also serve partly as vehicles for the acid dyes that are employed in this invention. These alcohols generally alter the hydrophobic or hydrophilic character of the skin and permit good penetration of the acid dyes into the skin. A number of alcohols are known which may be utilized in this invention. By way of illustrating the alcohols mention may be made of benzyl alcohol, n-pentanol, ethanol, butanol and mixture thereof.

Exceptionally good results in skin toning have been obtained with certain combinations of alcohols that are employed in certain defined ratio ranges. These include such systems as benzyl alcohol/ethanol, n-butanol/ethanol. Typical alcohol systems and the ratio by volume of each system is given in Table III below:

TABLE III

| ALCOHOL SYSTEM | GENERAL RATIOS | PREFERRED RATIO |
|---|---|---|
| benzyl alcohol/ethanol | 1:5 to about 2:1 | 1:2 to about 1:1 |
| n-pentanol/ethanol | 1:6 to about 2.5:1 | 1:3 to about 1:1 |
| n-butanol/ethanol | 1:8 to about 3:1 | 1:8 to about 1:1 |

The quantity of alcohol system used as skin penetrating agent according to the present invention may vary according to the particular alcohol or alcohols employed. Generally, this will vary from about 1% to about 40% by weight based on the total weight of the composition. In a preferred aspect of this invention this range will be from about 1% to about 8% on the same weight basis.

The compositions of the present invention have a pH on the acid side which is generally equal to or less than about 4. However, the preferred pH range will usually be from about pH 2 to about pH 4. This pH being maintained by a buffer system. A citrate buffer adjusted to the appropriate pH with sodium hydroxide has been found t be quite suitable.

When the composition takes the form of a solution the balance of the composition will usually be made up with water. Generally, water will comprise between about 50% and about 95% by weight based on the total weight of these compositions.

It may sometimes be advantageous to include in the composition of the present invention one or more thickening agents. This is done to avoid excessive dripping when the product is applied to the skin. A material that has been found to be particularly useful for this purpose is hydroxyethyl cellulose. When a thickening component is incorporated in this composition it will generally comprise from about 0.1% to about 5% by weight based on the total weight of the composition., In addition other optional auxiliary agents may form part of this composition which serve to improve its organoleptic properties or facilitate its application.

The compositions of this invention may take a variety of forms. Typical of these forms are as solutions, lotions, creams, gels, mousses, etc.

The manner in which the compositions of the present invention are used to a large extent depends on the results that are desired. Thus when employed to obtain a complete bronzing of the skin it will be used somewhat differently than when it is to affect spot changes. In addition the depth of color change desired will also influence how composition is employed.

Whether the product be in the form of a lotion, cream or gel, the mode of application can be as follows: In applying such product to the face for example, dab a small amount onto the fingertips, apply to an area of the face and repeat until product has been applied to entire face (and neck). The product may be re-applied if a deeper, darker tone is desired. Also, after one minute, the product may be rinsed with water, if so desired without affecting the imparted color.

The product could also be applied using a *face styling sponge* instead of the fingertips.

When it is desired to remove the present product from the skin this can be accomplished by washing with soap and water using a face cloth, sponge or one's bare hand.

To evaluate the coloring developed on skin employing the present invention color measurements were made using the LabScan Spectrocolorimeter available from Hunter Associates Laboratory, Inc. of Reston, Va. The results are given in terms of the Hunter L, a and b values which are defined as follows:

L - measures lightness and varies from 100 for perfect white to zero for black (approximately as the eye would evaluate it).

The chromaticity dimensions, a and b, give designations of color a follows:

a - measures redness when plus, gray when zero, and greenness when minus b - measures yellowness when plus, gray when zero, and blueness when minus.

During certain evaluations involving color measurements, color-difference becomes an important consideration. Color difference is calculated using the L, a, b scale and, since all three values are used in the computation, it is generally referred to as Total Color Difference (E), $$E = \sqrt{(\Delta L)^2 + (\Delta a)^2 + (\Delta b)^2} \quad (1)$$

where
$\Delta L = L_{SMP} - L_{STD}$
 (if $+\Delta L$, sample is lighter than standard
 if $-\Delta L$, sample is darker than standard)
$\Delta a = a_{SMP} - a_{STD}$
 (if $+\Delta a$, sample is redder than standard
 if $-\Delta a$, sample is greener than standard)
$\Delta b = b_{SMP} - b_{STD}$
 (if $+\Delta b$, sample is yellower than standard
 if $-\Delta b$, sample is bluer than standard The following examples are given to further illustrate the present invention. It is understood, however, that it is not limited thereto.

Skin dyeing studies were conducted using skin toner composition of Example 1 (Toner No. 2), Example 2 (Toner No. 3), Example 3 (Toner No. 4) and Example 4 (Toner No. 7). Evaluation of these compositions for skin bronzing was performed on the fore arm skin of Caucasian subjects. Five milliliters (~5g) of each product was applied to the test site of inner forearm (total surface area of 15.5cm²) and left on for 15 seconds or one minute. The test site was then rinsed thoroughly under lukewarm running tap water.

The change in skin color obtained by this treatment was measured using the LabScan LS-5100 Spectrocolorimeter and the color changes reported expressed as Hunter L, a, b values and discussed in more detail below.

Further examples of compositions embodied in the present invention are given in tabular form below in Table V. Toner #7M is a thickened formulation having a gel-like consistency This was prepared using a laboratory stirrer and the product was stirred continuously to ensure uniformity. A 500 gram batch of this product was made using the following procedure: Weigh 250 grams of hot water (approx. 70° C.) into a beaker. Slowly add 12.5 g of Cellosize (thickener). A clear gel will form Add 50 ml of 0.5 M citrate/NaOH Buffer pH 3. Add the dyes which were previously solubilized in approx. 40-50 ml of hot water. Preservatives can be added next, for example, methylparaben (0.75 g) and propylparaben (0.25 g) By now, the batch will have cooled somewhat and the alcohols can be added (40 ml of Benzyl Alcohol/Ethanol solution - 40:60 by volume). Finally, Qs the batch to 500 grams with water and stir until of uniform consistency.

Toners 4, 27, 28, 35 and 39 were prepared as described above except the step involving addition of the thickener was omitted.

TABLE IV

Composition of Skin Toners

| Ingredients | EXAMPLE 1 Toner No. 2 | EXAMPLE 2 Toner No. 3 | EXAMPLE 3 Toner No. 4 | EXAMPLE 4 Toner No. 7 |
|---|---|---|---|---|
| Dyes | | | | |
| FD & C D & C Violet No. 2 | 0.0706 g | 0.0350 g | 0.0355 g | 0.0504 g |
| FD & C Orange No. 4 | 0.3011 g | 0.3005 g | 0.3009 g | 0.1600 g |
| FD & C Yellow No. 6 | 0.0255 g | 0.0253 g | 0.0165 g | 0.0250 g |
| FD & C Blue No. 1 | — | 0.0165 g | 0.0165 g | 0.0256 g |
| Other | | | | |
| Ethanol SDA-40 | 40 ml | 40 ml | — | — |
| Citrate Buffer* | 10 ml | 10 ml | 10 ml | 10 ml |
| Benzyl Alcohol/Ethanol** | — | — | 8 ml | 8 ml |
| Water | qs | qs | qs | qs |
| TOTAL | 100 ml | 100 ml | 100 ml | 100 ml |

*0.5 citrate buffer adjusted to pH 3 with NaOH
**40% solution of benzyl alcohol in ethanol (by volume)

TABLE V

| Ingredients | Ex. 5 Toner #4 | Ex. 6 Toner #7M | Ex. 7 Toner #27 | Ex. 8 Toner #28 | Ex. 9 Toner #35 | Ex. 10 Toner #39 |
|---|---|---|---|---|---|---|
| Dyes: | | | | | | |
| Ext. D & C Violet #2 | 0.0355 g | 0.0253 g | 0.0040 g | 0.0100 g | 0.0250 g | 0.0400 g |
| D & C Orange #4 | 0.3009 g | 0.0800 g | 0.0120 g | 0.0204 g | 0.0500 g | 0.0800 g |
| FD & C Yellow #6 | 0.0250 g | 0.0125 g | 0.0021 g | 0.0040 g | — | — |
| FD & C Blue #1 | 0.0165 g | 0.0130 g | 0.0025 g | 0.0042 g | 0.0107 g | — |
| FD & C Red #4 | — | 0.0109 g | 0.0020 g | 0.0030 g | 0.0103 g | — |
| FD & C Yellow #5 | — | — | — | — | 0.0050 g | — |
| D & C Green #5 | — | — | — | — | — | 0.0600 g |
| Other: | | | | | | |
| Citrate buffer (0.5 M, pH 3) | 10 ml | 10 ml | 10 ml | 10 ml | 10 ml | 10 ml |
| Benzyl alcohol/ethanol* | 8 ml | 8 ml | 8 ml | 8 ml | 8 ml | 8 ml |
| Cellosize | | 2.5 g | | | | |

TABLE V-continued

| Ingredients | Ex. 5 Toner #4 | Ex. 6 Toner #7M | Ex. 7 Toner #27 | Ex. 8 Toner #28 | Ex. 9 Toner #35 | Ex. 10 Toner #39 |
|---|---|---|---|---|---|---|
| Methylparaben | | 0.15 g | | | | |
| Propylparaben | | 0.05 g | | | | |
| Water | q. s. | q. s. | q. s. | q. s. | q. s. | q. s. |
| TOTAL | 100 ml | 100 ml | 100 ml | 100 ml | 100 ml | 100 ml |

*40% solution of benzyl alcohol in ethanol (by volume)

The products of Examples 5 through 10 were applied to Caucasian skin using the process given above in this connection with the products of Examples 1 through 4 except for the toner 7M which was applied to the skin but in quantity of only 0.2g.

A feature of the present invention is the fact that bronzing effects on skin that are obtained with compositions of this invention are more resistant to wash-off by water when compared to typical commercial products that are available for this or similar purposes. This has been demonstrated first by measuring the color of the skin using the LabScan Spectrocolorimeter and reporting the color by the Hunter values L, a and b described above.

The respective products were applied to Caucasian skin under standardized conditions and then rinsed with water briefly to the same extent. The same color measurements were again made and from this the changes in the Hunter values ( L, a and b) were calculated. From this data the Total Color Difference (E) was calculated using formula (1) above; the larger the value of E the more resistant the product is to wash-off by water.

The results of these studies are summarized in Tables VI and VII below. Tables VI being directed to the use of commercially available products and VII to typical products of this invention namely skin toner composition 2, 3, 4 and 7 (See Examples 1–4 of Table IV for formulations). It will be noted that for all the products representative of this invention the Total Color Difference (E) was greater than the corresponding value for the commercial products.

TABLE VI

Effect of Commercially Available Bronzing Products on the Color Changes of Caucasian Skin

| Product Tested | Type of Product | Test No. | Skin Color Initial | | | Skin Color After Application And Water Rinse | | | Difference in Skin Color Due to Product Use | | | Total Color Difference |
|---|---|---|---|---|---|---|---|---|---|---|---|---|
| | | | L | a | b | L | a | b | Δ L | Δ a | Δ b | (E) |
| Aramis | B | 1 | 63.66 | 6.89 | 11.39 | 59.98 | 8.55 | 9.82 | −3.68 | 1.66 | −1.57 | 4.33 |
| | | 2 | 62.59 | 6.65 | 11.46 | 59.99 | 9.25 | 10.02 | −2.60 | 2.60 | −1.44 | 3.95 |
| Halston Z-14 | B | 1 | 63.74 | 5.74 | 11.65 | 57.96 | 9.49 | 10.48 | −5.78 | 3.75 | −1.17 | 6.99 |
| | | 2 | 61.41 | 7.52 | 10.76 | 59.85 | 8.53 | 10.43 | −1.56 | 1.01 | −0.33 | 1.89 |
| Clinique | B | 1 | 63.00 | 6.62 | 11.28 | 62.16 | 6.89 | 10.50 | −0.84 | 0.27 | −0.78 | 1.18 |
| | | 2 | 62.81 | 6.21 | 11.12 | 60.72 | 8.76 | 9.87 | −2.09 | 2.55 | −1.25 | 3.53 |
| Revlon Pure Radiance | M | 1 | 63.31 | 6.42 | 11.07 | 60.26 | 9.42 | 11.31 | −3.05 | 3.00 | 0.24 | 4.28 |
| | | 2 | 62.97 | 6.78 | 11.27 | 62.27 | 7.21 | 11.28 | −0.70 | 0.43 | 0.01 | 0.82 |
| Bonne Bell | B | 1 | 63.55 | 6.09 | 11.53 | 59.55 | 9.52 | 10.86 | −4.00 | 3.43 | −0.67 | 5.31 |
| | | 2 | 62.03 | 6.55 | 11.13 | 60.60 | 9.00 | 10.56 | −1.43 | 2.45 | −0.57 | 2.89 |
| Royal Copenhagen | B | 1 | 63.34 | 7.23 | 11.39 | 60.88 | 9.34 | 10.27 | −2.46 | 2.11 | −1.12 | 3.43 |
| | | 2 | 61.85 | 6.63 | 10.92 | 59.19 | 9.40 | 10.24 | −2.66 | 2.77 | −0.68 | 3.90 |

B — Bronzer
M — Makeup

TABLE VII

Effect of Skin Toners on the Color Changes of Caucasian Skin

| Subject No. | Skin Toner | Treatment Time (Min.) | Skin Color Initial | | | Skin Color After Application and Water Rinse | | | Difference in Skin Color Due To Product Usage | | | Total Color Difference |
|---|---|---|---|---|---|---|---|---|---|---|---|---|
| | | | L | a | b | L | a | b | Δ L | Δ a | Δ b | (E) |
| 1 | No. 2 | 0.25 | 63.57 | 6.61 | 10.53 | 46.54 | 17.63 | 13.44 | −17.04 | 11.01 | 2.91 | 20.49 |
| 1 | No. 2 | 1.0 | 63.52 | 6.96 | 10.37 | 45.36 | 17.77 | 13.24 | −18.16 | 10.80 | 2.88 | 21.33 |
| 1 | No. 3 | 1.0 | 63.10 | 6.15 | 10.97 | 51.90 | 14.04 | 14.44 | −11.20 | 7.91 | 3.47 | 14.14 |
| 1 | No. 4 | 1.0 | 63.96 | 7.13 | 11.62 | 40.95 | 21.86 | 17.56 | −23.02 | 14.73 | 5.94 | 27.96 |
| 1 | No. 7 | 0.25 | 63.95 | 5.61 | 11.44 | 47.68 | 14.89 | 13.11 | −16.26 | 9.28 | 1.67 | 18.80 |
| 1 | No. 7 | 1.0 | 64.64 | 5.51 | 10.62 | 41.69 | 15.90 | 12.28 | −22.95 | 10.39 | 1.67 | 25.24 |
| 2 | No. 7 | 0.25 | 55.93 | 7.50 | 14.76 | 41.06 | 13.98 | 14.21 | −14.87 | 6.47 | −0.55 | 16.23 |
| 2 | No. 7 | 1.0 | 55.08 | 6.99 | 15.12 | 34.58 | 14.42 | 13.40 | −20.50 | 7.43 | −1.72 | 21.87 |

What is claimed is:
1. A process for coloring skin which comprises the step of contacting the skin with a solution consisting of
(a) an alcohol component which is capable of penetrating the skin to alter the hydrophobic or hydrophilic structures thereof;
(b) a water soluble acid dye component wherein the dye is at least one selected from the group consisting of dyes having the formula:

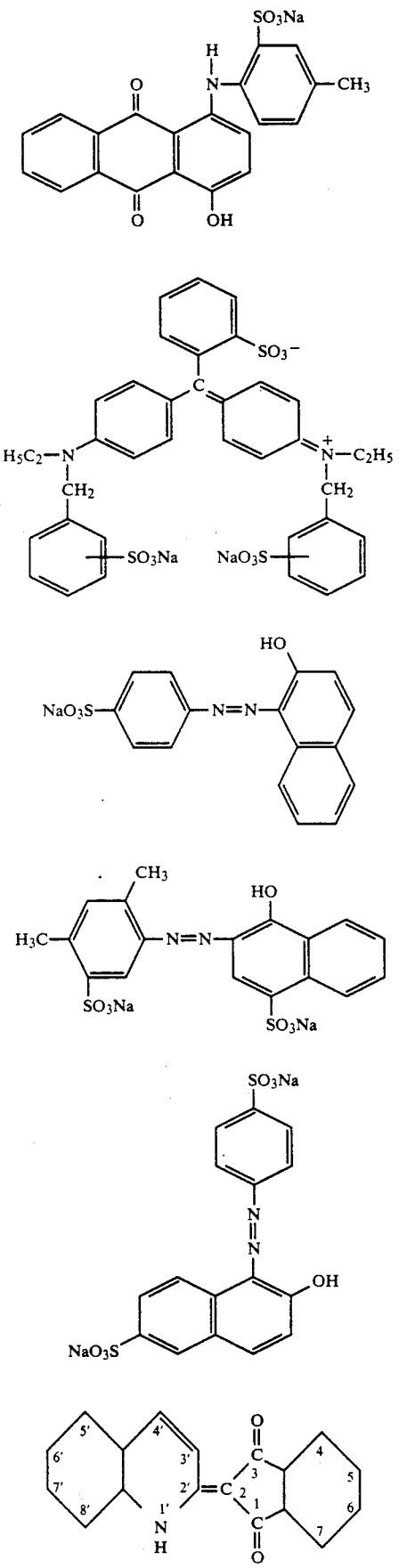

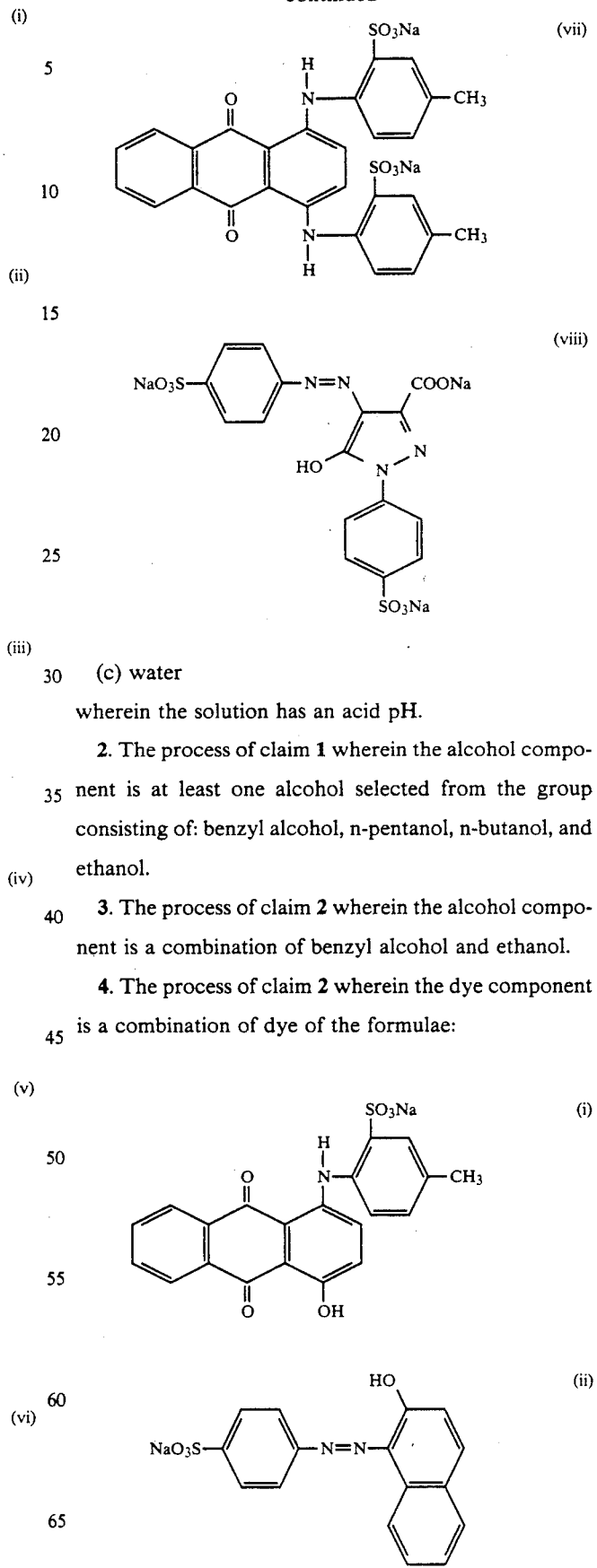

(c) water wherein the solution has an acid pH.

2. The process of claim 1 wherein the alcohol component is at least one alcohol selected from the group consisting of: benzyl alcohol, n-pentanol, n-butanol, and ethanol.

3. The process of claim 2 wherein the alcohol component is a combination of benzyl alcohol and ethanol.

4. The process of claim 2 wherein the dye component is a combination of dye of the formulae:

-continued
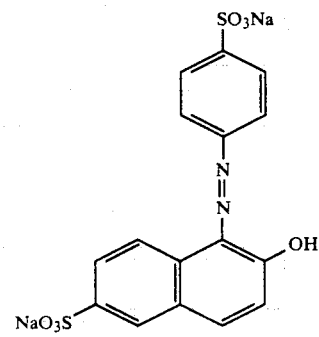
(iii)
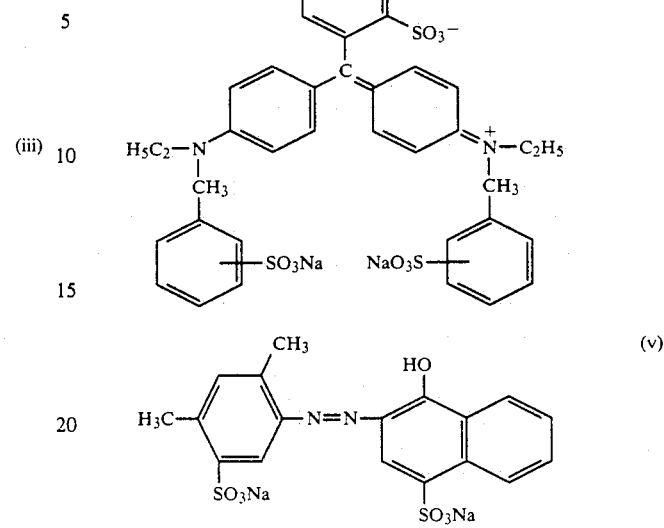
(iv)
(v)
* * * * *